United States Patent [19]

Sharp

[11] 4,128,715
[45] Dec. 5, 1978

[54] CEPHALOSPORIN ANTIBIOTICS

[75] Inventor: Christopher J. Sharp, Northolt, England

[73] Assignee: Glaxo Laboratories Limited, Greenford, England

[21] Appl. No.: 791,529

[22] Filed: Apr. 27, 1977

[30] Foreign Application Priority Data

Apr. 28, 1976 [GB] United Kingdom ............... 17307/76

[51] Int. Cl.$^2$ ......................................... C07D 501/20
[52] U.S. Cl. ...................................... 544/22; 424/246
[58] Field of Search ....................... 260/243 C; 544/22

[56] References Cited

U.S. PATENT DOCUMENTS

| 3,974,153 | 8/1976 | Cook et al. | 260/243 C |
| 3,984,403 | 10/1976 | Fujisawa et al. | 260/243 C |

Primary Examiner—Nicholas S. Rizzo
Attorney, Agent, or Firm—Bacon & Thomas

[57] ABSTRACT

A special crystalline form of the L-lysine salt of the antibiotic cefuroxime is described. The salt has improved properties that permit it to be used in areas where cefuroxime itself and known derivatives of cefuroxime cannot be used.

1 Claim, 1 Drawing Figure

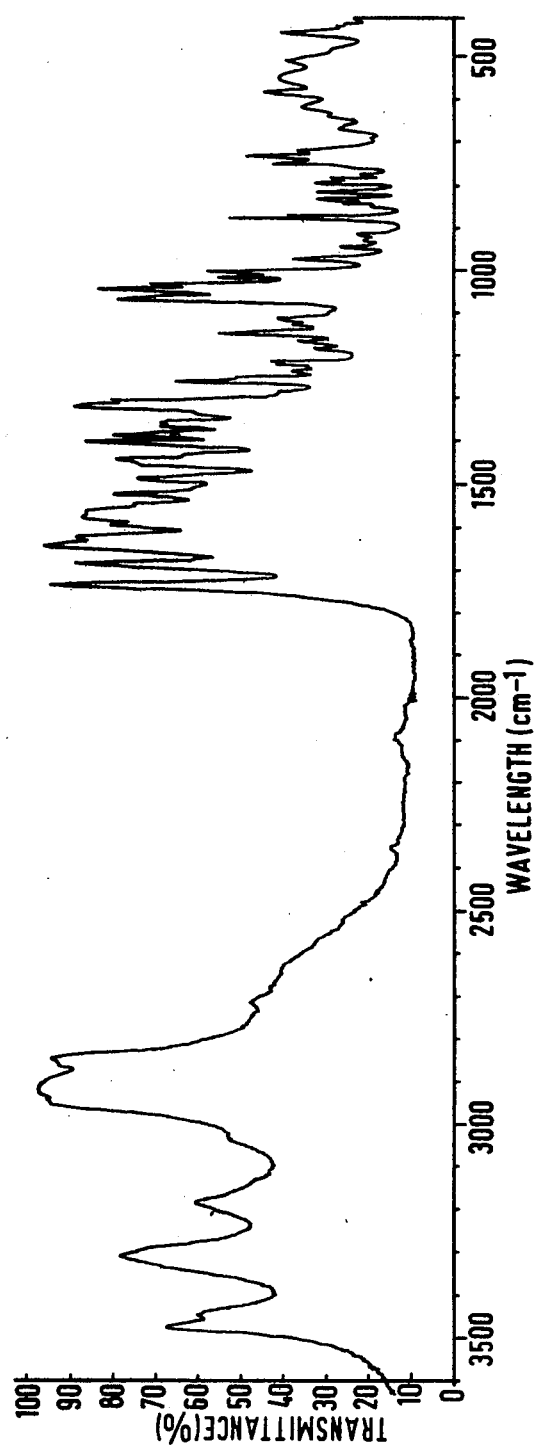

CEPHALOSPORIN ANTIBIOTICS

This invention is concerned with improvements in or relating to cephalosporin antibiotics. More particularly the invention is concerned with salts of the cephalosporin antibiotic (6R,7R)-3-carbamoyloxymethyl-7-[(2Z)-2-(fur-2-yl)-2-methoxyiminoacetamido] ceph-3-em-4-carboxylic acid, which has the approved name 'cefuroxime'.

Cefuroxime, as described and claimed in British Patent Specification No. 1,453,049 is a valuable broad spectrum antibiotic characterised by high activity against a wide range of gram-positive and gram-negative microorganisms, this property being enhanced by the very high stability of the compound to $\beta$-lactamases produced by a range of gram-negative microorganisms. Additionally the compound is stable in the body owing to its resistance to the action of mammalian esterases, and gives high serum levels following parenteral administration to human and animal subjects, while exhibiting low serum binding.

Cefuroxime may be administered, in human or veterinary medicine, as a non-toxic derivative, i.e. one which is physiologically acceptable in the dosage at which it is administered. Such non-toxic derivatives conveniently include those salts, e.g. alkali metal, alkaline earth metal and organic base salts which on admixture with sterile, pyrogen-free water form aqueous solutions or suspensions for injection. In British Patent Specification No. 1,453,049 the sodium salt of cefuroxime is described as being a substance well suited to administration on injection. A number of different crystalline forms of sodium cefuroxime have been discovered and the particular form obtained is dependent upon the medium and isolation technique employed in crystallising the salt.

However, the solubility of sodium cefuroxime has presented difficulty in formulating a relatively concentrated aqueous solution containing the desired dosage of cefuroxime. It is desirable to be able to form such solutions for use on those occasions, e.g. intramuscular administration, when it is necessary to give cefuroxime at high dosage levels to combat the invading microorganism.

In an endeavour to obtain derivatives of various $\beta$-lactam antibiotics having improved pharmaceutical properties over such commonly investigated substances as salts formed with alkali metals, various investigators have studied those salts formed with basic amino acids. Thus, by way of example, according to British Patent Specification No. 1,418,149 salts of cephalosporin antibiotics (so-called 'acid cephalosporins') with arginine or lysine are stated to possess, inter alia, an enhanced degree of solubility and an increased rate of dissolution in water at room temperature as compared with the corresponding sodium salts. It is also stated that such salts possess 'higher stability'.

In the specific case of cefuroxime we have discovered that arginine and lysine can form salts possessing relatively poor solid state stability and/or solubility in an aqueous medium little different from that of sodium cefuroxime.

In particular we have found that the L-lysine salt of cefuroxime (a previously unreported salt) can exist (a) in at least three crystalline forms, (b) as a gel and (c) in a lyophilised state. Of these, we have found that only one, a specific crystalline form which we have designated "Form II", exhibits an improved balance of properties, viz high solubility and rapid rate of solution in water (even at a temperature as low as 15° C.) and good solid state stability, as compared with sodium cefuroxime. Furthermore, and very surprisingly, the Form II salt when dissolved in water, is not readily converted to a less soluble crystalline form even after seeding with that less soluble form.

Form II of the lysine salt of cefuroxime is characterised by possessing the X-ray diffraction data given in Example 1 below. It also possesses characteristic solid state infrared spectroscopic data which is also given in Example 1.

The properties of Form II may be compared with those of other salts of cefuroxime e.g. sodium cefuroxime, by the following methods:

SOLUBILITY AND RATE OF SOLUTION

Cefuroxime salt (equivalent to 1.0 g of cefuroxime L-lysine salt) is weighed into a 10 ml vial. Carbon dioxide-free distilled water (1.7 ml) is added. The sample is shaken for one minute. In the case of Form II a clear solution is achieved in no more than 1 minute at about 20° C.

SOLID STATE STABILITY

Cefuroxime salt (about 0.7 g) is stored at 50° C. for 14 days in a 5 ml capped vial and the sample is then compared with a sample of the same batch which has been stored for the same period at about −20° C. by (a) a main peak high pressure liquid chromatography assay
(b) a microbiological assay
(c) a colorimetric comparison of 10% m/v solutions in carbon dioxide free-distilled water.

PREPARATION

The L-lysine salt of cefuroxime is prepared by contacting L-lysine (or a simple derivative thereof) with cefuroxime (or a simple derivative thereof) in a solvent medium and recovering the salt in the desired form. In general, equimolar proportions of L-lysine and cefuroxime should be employed and salt formation may normally be effected at a temperature selected within the range of −30° to +100° C. The procedure for manufacturing Form II is governed by a number of factors and the temperature, the solvent medium and the method of contacting the reactants as well as the method of isolation are all important. The choice of solvent medium is particularly critical but a variety of preparative techniques may be employed.

The precise conditions under which Form II is formed are empirical and one can only give a number of apparently unrelated methods which have been found, as a matter of practice, to be suitable.

For instance, when propan-1-ol or propan-2-ol is used to precipitate the L-lysine salt of cefuroxime from an aqueous medium, e.g. aqueous propan-1-ol or water, at temperatures below 40° C. and preferably not greater than 25° C., Form II is obtained. If, however, the aqueous solution containing the L-lysine salt of cefuroxime is added to propan-1-ol or propan-2-ol even at elevated temperatures, e.g. from 40°–80° C., Form II is still obtained.

Form II may also be formed in other ways, for example by precipitation from an aqueous solution with acetone at temperatures of −10° to +10° C. e.g. when an aqueous solution containing the L-lysine salt of cefuroxime is cooled in an ice-bath and acetone is added to induce precipitation of the desired crystalline form. A further method which may be used to produce Form II is to contact L-lysine and cefuroxime in aqueous ethanol and add the resultant aqueous solution to ethanol, at a temperature of from +10° to +30° C., to cause precipitation.

Form II has proved to be readily isolatable and possesses a high degree of crystallinity as evidenced by inspection of X-ray powder photographs.

We prefer to isolate Form II substantially free from the other forms of the L-lysine salt of cefuroxime. It may however be convenient as a matter of industrial practice to isolate a mixture of Form II with a minor proportion, advantageously not more than 15%, and preferably not more than 10%, of another form.

Form II may be isolated under conditions such as to produce sterile material. Thus a sterilised solution of salt may be produced and precipitation of Form II therefrom may be effected under sterile conditions.

Form II is particularly suited for formulation for injection. It may be presented in unit dose form in ampoules or vials, or in multi-dose containers with added preservative. The Form II may be in powder form for reconstitution with a suitable vehicle, e.g. sterile, pyrogen-free water, before use. Alternatively, the composition may take the form of a suspension, solution or emulsion in an oily or aqueous vehicle, and may contain formulatory agents such as suspending, stabilising and/or dispersing agents.

In general the compositions may contain from 0.1% upwards, e.g. 0.1–99%, preferably from 10–60% of the Form II, depending on the type of composition. Where dosage units are used, each unit will preferably contain 50–1500 mg of the active ingredient (calculated as cefuroxime). The dosage as employed for adult human treatment will preferably range from 500–4000 mg per day, for instance 1500 mg per day (calculated as cefuroxime), depending on the route and frequency of administration.

The Form II L-lysine salt of cefuroxime may be administered in combination with other compatible therapeutic agents such as other antibiotics, for example compatible penicillins and compatible cephalosporins.

The following Examples illustrate the invention.

EXAMPLE 1

A solution of (6R,7R)-3-carbamoyloxymethyl-7-[(2Z)-2-(fur-2-yl)-2-methoxyiminoacetamido]ceph-3-em-4 carboxylic acid (4.24 g, 10 mmole) in a mixture of acetone (20 ml) and water (5 ml) was clarified by filtration and then cooled in an ice bath whilst a solution of L-lysine (1.46 g, 10 mmole) in water (3 ml) was added dropwise with stirring. During addition it was necessary to add more acetone (80 ml) to assist stirring the thick suspension. After completing the addition the precipitate was collected, washed with acetone and dried in vacuo for 16 hrs. at room temperature to give the L-lysine salt of cefuroxime Form II (5.19 g, 91% theory).

The product obtained is characterised by the following X-ray diffraction date:

Experimental details

Debye-Scherrer camera, diameter 114.6 mm., copper Kα radiation, 1.5418Å, nickel filtered. Intensities by visual comparison with calibrated standard lines. Sample contained in a sealed glass capillary tube. Material refrigerated at 2° C. prior to diffraction photography.

| Line number | d (Å) | Relative Intensity | Line number | d (Å) | Relative Intensity |
|---|---|---|---|---|---|
| 1 | 13.59 | 100 | 19 | 3.26 | 12 |
| 2 | 10.46 | 80 | 20 | 3.18 | 12 |
| 3 | 9.18 | 16 | 21 | 3.06 | 19 |
| 4 | 8.40 | 75 | 22 | 2.97 | 10 |
| 5 | 6.88 | 56 | 23 | 2.82 | 14 |
| 6 | 6.31 | 16 | 24 | 2.78 | 7 |
| 7 | 5.80 | 2 | 25 | 2.69 | 4 |
| 8 | 5.48 | 6 | 26 | 2.64 | 17 |
| 9 | 5.23 | 14 | 27 | 2.47 | 6 |
| 10 | 4.79 | 52 | 28 | 2.38 | 8 |
| 11 | 4.74 | 40 | 29 | 2.32 | 6 |
| 12 | 4.58 | 16 | 30 | 2.25 | 9 |
| 13 | 4.41 | 76 | 31 | 2.03 | 4 |
| 14 | 4.11 | 40 | 32 | 1.99 | 2 |
| 15 | 3.98 | 52 | 33 | 1.95 | 1 |
| 16 | 3.82 | 16 | 34 | 2.10 | 1 |
| 17 | 3.61 | 71 | 35 | 1.90 | 4 |
| 18 | 3.42 | 17 | 36 | 1.81 | 5 |

The product also possesses the following infrared spectroscopic data:

| | | |
|---|---|---|
| 3485 w | 1586 s | 1270 w |
| 3456 w | 1564 m | 1158 w |
| 3320 m | 1535 m | 1075 m |
| 3195 w | 1496 w | 1055 m |
| 2725 w | 1410 s | 1042 w |
| 1746 s | 1396 m | 1025 w |
| 1696 s | 1365 w | 1012 w |
| 1655 s | 1330 s | 885 w |
| 1636 s | 1318 m | 742 w |
| 1605 m | | |

Key
s = strong
m = medium
w = weak
Spectrometer - Perkin Elmer 521, range 4000–650 $cm^{-1}$, Spectrum recorded for Nujol mull (bands associated with Nujol are excluded) taking care to avoid excessive grinding.

The accompanying drawing is a reproduction of the infrared spectrum of Form II.

EXAMPLE 2

L-lysine (0.73 g, 5 mmoles) was dissolved in water (8 ml) and (6R,7R)-3-carbamoyloxymethyl-7-[(2Z)-2-(fur-2-yl)-2-methoxyiminoacetamido]ceph-3-em-4-carboxylic acid (2.12 g, 5 mmole) was added and stirred until all had dissolved. The solution was filtered through kieselguhr and propan-1-ol(100 ml) was added dropwise with stirring over a period of 20 mins. and stirring was continued for a further 10 mins. The product was collected by filtration, washed well with propan-1-ol and then with ether and dried overnight in vacuo to give the salt, Form II (2.46 g, 86.3% theory), confirmed by infrared spectroscopy.

EXAMPLE 3

L-lysine monohydrochloride (4.56 g, 25 mmole) in distilled water (20 ml) was treated with triethylamine (3.5 ml, 25 mmole) and propan-2-ol (12 ml) and (6R,7R)-3-carbamoyloxymethyl-7-[(2Z)-2-(fur-2-yl)-2-methoxyiminoacetamido]ceph-3-em-4-carboxylic acid (10.6 g, 25 mmole) was added. The mixture was stirred until a clear solution was obtained.

The solution was added dropwise with stirring to propan-2-ol (400 ml) over a period of 30 mins. After ageing for 1 hr. at room temperature the solid was collected by filtration, washed with propan-2-ol (100 ml) and dried in vacuo at about 20° C. to give the salt, Form II (13.8 g, 96.8% theory) confirmed by infrared spectroscopy.

EXAMPLE 4

L-Lysine monohydrochloride (4.56 g, 25 mmole) in distilled water (20 ml) was treated with triethylamine (3.5 ml, 25 mmole), and ethanol (12 ml) and (6R,7R)-3-carbamoyloxymethyl-7-[(2Z)-2-(fur-2-yl)-2-methoxyiminoacetamido]ceph-3-em-4-carboxylic acid (10.6 g, 25 mmole) was added. The mixture was stirred until a clear solution was obtained.

The solution was added dropwise with stirring to ethanol (400 ml) over a period of 20 minutes. The precipitate was aged for 1 hour at about 20° C., the solid filtered off, washed with ethanol (100 ml) and dried in vacuo at about 20° C. to give the salt, Form II (12.5 g, 87.8% theory), confirmed by infrared spectroscopy.

Pharmaceutical Composition — Dry Powder for Injection

Sterile L-lysine salt of cefuroxime Form II is filled into glass vials, the stated contents of each container being either 500 mg or 1.00 g of cefuroxime. Filling is carried out aseptically under a blanket of sterile nitrogen. The vials are closed using rubber discs or plugs, held in position by aluminium sealing rings, thereby preventing gaseous exchange or ingress of micro-organisms. The product may be constituted by dissolving in Water for Injections (1.5 to 2.0 ml and 3.0 to 4.0 ml respectively) or other suitable sterile vehicle shortly before administration.

I claim:

1. The crystalline form of L-lysine salt of cefuroxime characterised by the following X-ray diffraction data:

| Line number | d (Å) | Relative Intensity | Line number | d (Å) | Relative Intensity |
|---|---|---|---|---|---|
| 1 | 13.59 | 100 | 19 | 3.26 | 12 |
| 2 | 10.46 | 80 | 20 | 3.18 | 12 |
| 3 | 9.18 | 16 | 21 | 3.06 | 19 |
| 4 | 8.40 | 75 | 22 | 2.97 | 10 |
| 5 | 6.88 | 56 | 23 | 2.82 | 14 |
| 6 | 6.31 | 16 | 24 | 2.78 | 7 |
| 7 | 5.80 | 2 | 25 | 2.69 | 4 |
| 8 | 5.48 | 6 | 26 | 2.64 | 17 |
| 9 | 5.23 | 14 | 27 | 2.47 | 6 |
| 10 | 4.79 | 52 | 28 | 2.38 | 8 |
| 11 | 4.74 | 40 | 29 | 2.32 | 6 |
| 12 | 4.58 | 16 | 30 | 2.25 | 9 |
| 13 | 4.41 | 76 | 31 | 2.03 | 4 |
| 14 | 4.11 | 40 | 32 | 1.99 | 2 |
| 15 | 3.98 | 52 | 33 | 1.95 | 1 |
| 16 | 3.82 | 16 | 34 | 2.10 | 1 |
| 17 | 3.61 | 71 | 35 | 1.90 | 4 |
| 18 | 3.42 | 17 | 36 | 1.81 | 5 |

* * * * *